United States Patent [19]

Kennedy et al.

[11] Patent Number: 4,806,663

[45] Date of Patent: Feb. 21, 1989

[54] CERTAIN 3-SUBSTITUTED 2-ALKYL BENZOFURAN DERIVATIVES

[75] Inventors: Thomas P. Kennedy, Memphis; George W. Kabalka, Knoxville, both of Tenn.

[73] Assignee: The University of Tennessee Research Corporation, Knoxville, Tenn.

[21] Appl. No.: 35,049

[22] Filed: Apr. 6, 1987

[51] Int. Cl.$^4$ ............................................. C07D 307/81
[52] U.S. Cl. ................................... 549/471; 544/153; 546/196; 548/525
[58] Field of Search ............... 514/236, 237, 320, 422, 514/469; 544/153; 546/196; 548/525; 549/471

[56] References Cited

U.S. PATENT DOCUMENTS

| | | | |
|---|---|---|---|
| 3,248,401 | 4/1966 | Tondeur et al. | 260/346.2 |
| 3,627,763 | 12/1971 | Jaeggi et al. | 260/247.7 |
| 3,810,991 | 5/1974 | Binon et al. | 424/263 |
| 3,818,035 | 6/1974 | Binon | 260/309.6 |
| 3,891,648 | 6/1975 | Descamps et al. | 260/268 BC |
| 3,917,600 | 11/1975 | Descamps et al. | 260/268 |
| 3,920,707 | 11/1975 | Descamps et al. | 260/346.2 R |
| 3,929,836 | 12/1975 | Fothergill et al. | 260/346.2 R |
| 3,931,240 | 1/1976 | Binion et al. | 260/346.2 R |
| 3,972,900 | 8/1976 | Fothergill et al. | 260/346.2 R |
| 4,007,204 | 2/1977 | Descamps et al. | 260/330.5 |
| 4,485,112 | 11/1984 | Pestellini et al. | 424/285 |

OTHER PUBLICATIONS

"The Condensed Chemical Dictionary", 6th Ed., Reinhold, p. 41 (1961).
Title: Medical Intelligence Drug Therapy—Amiodarone Author: Jay W. Mason Publication: The New England Journal of Medicine, vol. 316, No. 8, Feb. 19, 1987.
Spectroscopic Studies of Cutaneous Photosensitizing Agents—IX, A Spin Trapping Study of the Photolysis of Amiodarone and Desethylamiodarone, Anson S. W. Li and Colin F. Chingnell, Photochemistry and Photobiology, vol. 45, No. 2, pp. 191-197, Feb. 1987 Issue.
The Effect on Atrial and Ventricular Intracellular Potentials, and Other Pharmacological Actions of L9146, A Non-Halogenated Benzo(B)Thhiphene Related to Amiodarone, E. M. Vaughan Williams, L. Salako and H. Wittig, Cardiovascular Research, 1977, 11, 1870197.

*Primary Examiner*—Mary C. Lee
*Assistant Examiner*—Bernard I. Dentz
*Attorney, Agent, or Firm*—Luedeka, Hodges & Neely

[57] ABSTRACT

The disclosure relates to compounds of the formula

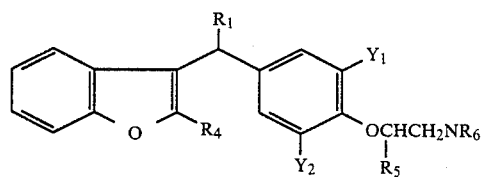

and pharmaceutically acceptable addition salts thereof wherein $R_1$ represents hydrogen, $R_1$ represents a group having the formula $-OR_2$ in which $R_2$ is a lower alkyl group or an aryl group, or $R_1$ represents a group having the formula

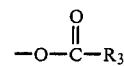

in which $R_3$ is hydrogen, a lower alkyl group, or an aryl group, wherein $R_4$ is a lower alkyl group containing 1 to 6 carbon atoms, wherein $R_5$ is either hydrogen or methyl, wherein $NR_6$ is a group selected from the class consisting of amino, lower mono and dialkylamino, piperidino, pyrrolidino, and morpholino groups and wherein $Y_1$ and $Y_2$ are identical and are hydrogen or a halogen. Compounds in accordance with the invention are useful as vasodilators and as antiarrythmic agents.

9 Claims, No Drawings

CERTAIN 3-SUBSTITUTED 2-ALKYL BENZOFURAN DERIVATIVES

The U.S. Government has rights in the invention disclosed and claimed in this application pursuant to NIOSH Grant No. R01-0H02264-01.

The invention relates to compounds having pharmacological activity and more particularly relates to novel pharmacologically active 3-substituted 2-alkyl benzofuran derivatives, and methods for their preparation.

Compounds in accordance with the invention are represented by the general formula:

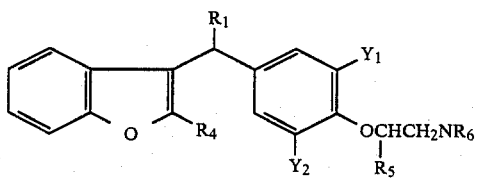

and pharmaceutically acceptable addition salts thereof wherein $R_1$ represents hydrogen, $R_1$ represents a group having the formula $-OR_2$ in which $R_2$ is a lower alkyl group or an aryl group, or $R_1$ represents a group having the formula

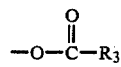

in which $R_3$ is hydrogen, a lower alkyl group, or an aryl group, wherein $R_4$ is a saturated lower alkyl group containing 1 to 6 carbon atoms, wherein $R_5$ is either hydrogen or methyl, wherein $NR_6$ is a group selected from the class consisting of amino, lower mono and dialkylamino, piperidino, pyrrolidino, and morpholino groups and wherein $Y_1$ and $Y_2$ are identical and are hydrogen or a halogen.

The term "lower alkyl" as used in this written description of the invention is intended, unless further defined, to designate a straight-chain, branched aliphatic hydrocarbon group containing between 1 to 18 carbon atoms, e.g. methyl, ethyl, isopropyl, tertiary butyl, and the like. "Aryl" refers to substituted or unsubstituted aromatic hydrocarbon groups, e.g., phenyl, naphthyl, benzyl, and the like. "Lower mono and dialkylamino" refers to amino groups with one or two straight-chain, or branched aliphatic hydrocarbon groups containing 1–6 carbon atoms. When two groups are present, they may be the same or different. Example are methylamino, dimethylamino, ethylamino, diethylamino, n-propylamino, isopropylamino, and the like. Halogen, unless further defined, is intended to refer to fluorine, chlorine, bromine, and iodine.

Compounds in accordance with the invention are useful as vasodialators and as antiarrythmic agents. Preferred for this purpose are compounds of the Formula I above wherein $R_1$ is hydrogen or $-OR_2$ with $R_2$ being a lower alkyl group containing between 1 and 6 carbon atoms, or $R_1$ is

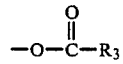

with $R_3$ being hydrogen, or a lower alkyl group containing between 1 and 6 carbon atoms, $R_4$ is butyl, $R_5$ is hydrogen, $NR_6$ is amino or lower mono and dialkylamino and $Y_1$ and $Y_2$ are identical and are hydrogen, bromine or iodine. Most preferably, $R_1$ is hydrogen or $-OR_2$ with $R_2$ being a lower alkyl group containing between 1 and 4 carbon atoms, or $R_1$ is

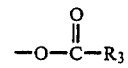

with $R_3$ being hydrogen or a lower alkyl group containing 1 to 4 carbon atoms, $R_4$ is n-butyl, $R_5$ is hydrogen, $NR_6$ is amino, ethylamino or diethylamino and $Y_1$ and $Y_2$ are either both hydrogen or both iodine.

The novel compounds of Formula I above are advantageously prepared by way of an alcohol intermediate which is produced by reducing a ketone of the formula:

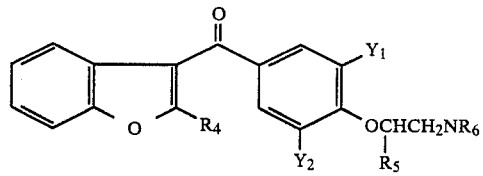

with $R_4$, $R_5$, $NR_6$, and $Y_1$ and $Y_2$ as defined for Formula I. Formula II ketones are known and procedures for their synthesis are described in U.S. Pat. No. 3,248,401, the disclosure of which is incorporated by reference. To produce compounds according to Formula I wherein $Y_1$ and $Y_2$ are identical halogens, reduction of the compounds of Formula II with $Y_1$ and $Y_2$ being halogens is performed under conditions which reduce the ketone group to the alcohol without otherwise affecting the molecule. A reducing system employing sodium borohydride in a tetrahydrofuran-methanol mixture (10:1 v/v) at approximately 0° C. produces high yields of the alcohol represented by Formula III:

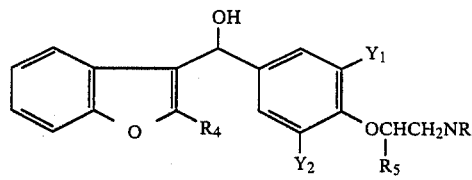

To prepare compounds of the invention wherein $Y_1$ and $Y_2$ are both hydrogen, the ketones of the Formula II wherein $Y_1$ and $Y_2$ are both hydrogen are similarly reduced to produce the alcohol intermediate shown in Formula IV. Alternately, reduction of Formula II compounds wherein $Y_1$ and $Y_2$ are both halogens employing a reduction system which reduces the ketone group to the alcohol while also dehalogenating the benzene ring produces Formula IV alcohols. Sodium borohydride in methanol in the presence of a $PdCl_2$ catalyst at 20° C. is a preferred reduction system to achieve both reduction and dehalogenation.

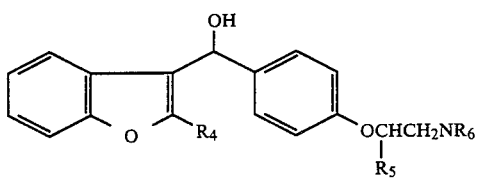

IV

Compounds of Formula I wherein $R_1$ is hydrogen are produced from the intermediates of Formulas II and IV by further reduction of the alcohol group. Compounds of Formula III (halogenated) or IV (dehalogenated), when reacted in a suitable solvent at 0° C. with sodium borohydride in trifluoroacetic acid produce compounds of Formulas V and VI, respectively.

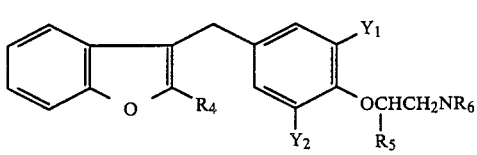

V

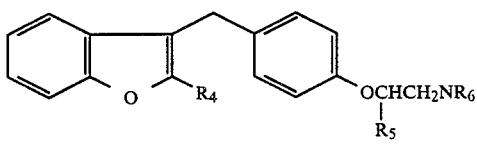

VI

The alcohols of Formulas III and IV are also employed as intermediates to produce compounds wherein $R_1$ is $-OR_2$ and $R_2$ is alkyl or aryl. A Williamson synthesis whereby the alcohols or Formula III or VI are converted to the corresponding alkoxide and reacted with an alkyl or aryl halide of the formula $R_2X$ is used to produce the ethers represented by Formulas VII (halogenated) and VIII (dehalogenated).

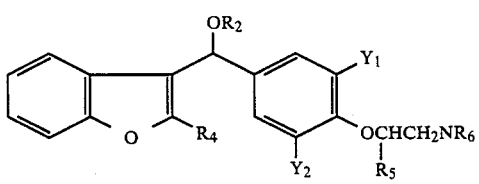

VII

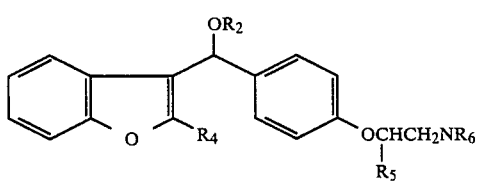

VIII

To produce the compounds of Formula I wherein $R_1$ is

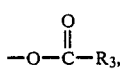

the alcohols of Formulas III and IV are esterified. Acyl halides of the formula

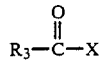

can be reacted with the alcohols of Formulas III or IV, respectively, preferably in the presence of a solvent capable of acting as an acid scavenger, e.g., pyridine, to produce compounds of Formulas IX (halogenated) or X (dehalogenated), respectively:

IX

X

The compounds of Formula I form acid addition salts with pharmaceutically acceptable salts, for example, with inorganic acids, such as hydrochloric acid, hydrobromic acid, sulphuric acid and phosphoric acid and with organic acids such as acetic acid, tartaric acid, maleic acid, citric acid and toluenesulfonic acid.

The compounds of the Formula I above and the salts thereof are useful in treating arrhythmic conditions and conditions for which treatment with a vasodialator is indicated. The novel pharmaceutically active agents provided by the present invention can be administered in pharmaceutical dosage forms, integrally, for example, parenterally or enterally with dosage adjusted to fit the exigencies of the therapeutic situation. The pharmaceutical dosage forms are prepared by incorporating the active ingredient in conventional liquid or solid vehicles to thereby provide emulsions, suspensions, tablets, capsules, powders and the like according to acceptable pharmaceutical practices. A wide variety of carriers or diluents as well as emulsifying agents, dispersing agents and other pharmaceutically acceptable adjuvants can be incorporated in the pharmaceutical dosage forms.

The following examples are offered to illustrate the invention and are not intended to be limiting.

EXAMPLE I

Preparation of (2-n-butyl-3-benzofuranyl)[4-[2-(diethylamino)ethoxyl]-3,5-diiodophenyl]methanol One 1 mmole (645 mg) of the ketone (2-n-butyl-3-benzofuranyl)[4-[2-(diethylamino)ethoxy]-3,5-diiodophenyl]methanone is dissolved in 30 ml of THF:MeOH (10:1 v/v). Sodium borohydride (1.2 mmole, 45.42 mg) is added to the solution and the mixture is stirred and maintained at a temperature of 0° C. until the starting material is consumed (~15 minutes). Excess borohydride is destroyed by the dropwise addition of water (0.5 ml). Volatile components are removed under reduced pressure (roto-evaporator). Water is added to the residue (~10 ml) followed by the addition of methylene chloride (~10 ml). The methylene chloride layer is separated from the aqueous phase and is dried over anhydrous sodium sulfate. The methylene chloride solvent is removed under reduced pressure and the product is purified by column chromatography (silica gel support using methylene chloride) and is recovered by reduced pressure evaporation of the methylene chloride. The yield of the product, m.p. 106°–107° C., is >50% of theoretical. (The m.p. of the hydrochloride salt is 143°–145° C.)

EXAMPLE II

Preparation of (2-n-butyl-3-benzofuranyl)[4-[2-(diethylamino)ethoxy]-phenyl]methanol One mmole (645 mg) of the ketone, (2-n-butyl-3-benzofuranyl)[4-[2-(diethylamino)ethoxyl]-3,5-diiodophenyl]methanone is dissolved in 10 ml of methanol. Palladium dichloride (2 mmole, 354 mg) is added and the mixture is agitated to suspend the palladium dichloride. The temperature of the mixture is adjusted to 20° C. Sodium borohydride (10 mmole, 379 mg) is added and stirring is continued until reaction is complete (~1 hour). The palladium dichloride is removed by filtration and water is added to the filtrate. An ether extraction is performed and the product is removed from the ether phase by evaporation under reduced pressure. The produce is purified by chromatography (silica gel using methylene chloride) and results in >50% yield of the product, m.p. 203° C. (decomposes).

EXAMPLE III

Preparation of (2-n-butyl-3-benzofuranyl)[4-[2-(diethylamino)ethoxyl]-3,5-diiodophenyl]methane One mmole (647 mg) of the alcohol as prepared in EXAMPLE I is dissolved in methylene chloride (5 ml). Sodium borohydride (38 mg, 10 mmole) added to 10 ml of trifluoroacetic acid and the mixture is cooled to 0° C. The methylene chloride solution is added slowly to the trifluoroacetic acid solution and the mixture stirred for 30 minutes at 0° C. Excess borohydride is destroyed by the dropwise addition of water (0.5 ml). Volatile components are removed under reduced pressure (rotoevaporator). Water is added to the residue (25 ml) followed by the addition of methylene chloride (25 ml). The methylene chloride layer is separated, washed twice with 25 ml of 5% aqueous sodium hydroxide and 25 ml of water. The methylene chloride solution is dried over sodium sulphate and then passed through a short (~5 cm) basic alumina column. Evaporation of the solvent yields the product, m.p. 80°–81° C., in >70% yield. (The m.p. of the hydrochloride salt is 119°–121° C.)

EXAMPLE IV

Preparation of methoxy(2-n-butyl-3-benzofuranyl)[4-[2-(diethylamino)ethoxyl]-3,5-diiodophenyl]methane One mmole (647 mg) of the alcohol as prepared in EXAMPLE I is dissolved in 10 ml of THF. The solution is cooled to −78° C. and lithium diisopropylamide in cyclohexane (1.1 mmole, 0.73 ml of a 1.5M solution) is slowly added. Methyl iodide (1.2 mmole, 0.17 g) is added and the mixture permitted to warm to room temperature (~30 minutes). The volatile components are removed under reduced pressure (rotoevaporator) and the residue is dissolved in methylene chloride. The methylene chloride solution is dried over anhydrous sodium sulfate and is purified by passing the solution through silica gel column as in EXAMPLE I. The product, m.p. 96°–98° C., is obtained upon evaporation of the solvent in a theoretical yield of >90%.

EXAMPLE V

Preparation of (2-n-butyl-3-benzofuranyl)[4-[2-(diethylamino)ethoxyl]-3,5-diiodophenyl]methyl pivalate One mmole (647 mg) of the alcohol as prepared in EXAMPLE I is dissolved in pyridine (4 ml). Excess pivaloyl chloride (5 mmole, 605 mg) is added to the pyridine solution and the mixture heated to 65° C. until the starting alcohol is completely consumed (approximately 12 hours). Volatile materials are removed under reduced pressure (roto-evaporator). The residue is dissolved in methylene chloride and the methylene chloride solution washed twice with 25 ml of 5% aqueous sodium hydroxide and once with 25 ml of water. The methylene chloride solution is dried over sodium sulfate and then passed through a short (~5 cm) basic alumina column. Evaporation of the solvent yields the product in >90% yield. (The m.p. of the hydrochloride salt is 108°–110° C.)

What is claimed is:

1. A compound of the formula:

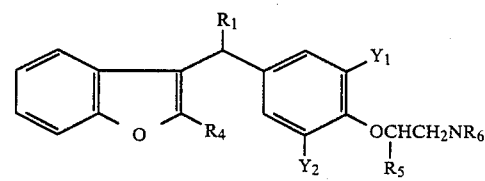

and pharmaceutically acceptable addition salts thereof wherein $R_1$ is selcted from the class consisting of hydrogen, a group having the formula $-OR_2$ in which $R_2$ is a lower alkyl group or an aryl group consisting of phenyl, naphthyl, and benzyl, and a group having the formula

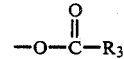

in which $R_3$ is hydrogen, a lower alkyl group, or an aryl group consisting of phenyl, naphthyl, and benzyl wherein $R_4$ is a lower aklyl group containing 1 to 6 carbon atoms, wherein $R_5$ is either hydrogen or methyl, wherein $NR_6$ is a group selected from the class consisting of amino, lower mono and dialkylamino, piperidino, pyrrolidino, and morpholino groups and wherein $Y_1$ and $Y_2$ are identical and are selected from the class consisting of hydrogen and halogen.

2. A compound as set forth in claim 1 wherein $R_1$ is selected from the class consisting of hydrogen, a group having the formula $-OR_2$ with $R_2$ being a lower alkyl group containing between 1 and 6 carbon atoms, and a group having the formula

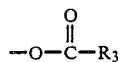

with $R_3$ being hydrogen or a lower alkyl group containing between 1 and 6 carbon atoms, $R_4$ is butyl, $R_5$ is hydrogen, $NR_6$ is selected from the class consisting of amino and lower mono and dialkylamino and $Y_1$ and $Y_2$ are identical and are selected from the class consisting of hydrogen, bromine, and iodine.

3. A compound as set forth in claim 1 wherein $R_1$ is selected from the class consisting of hydrogen, a group having the formula —$OR_2$ with $R_2$ being a lower alkyl group having between 1 and 4 carbon atoms, and a group having the formula

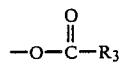

with $R_3$ being hydrogen or a lower alkyl group containing 1 to 4 carbon atoms, $R_4$ is n-butyl, $R_5$ is hydrogen, $NR_6$ is selected from the class consisting of amino, ethylamino, and diethylamino, and $Y_1$ and $Y_2$ are identical and are selected from the class consisting of hydrogen andd iodine.

4. A compoun according to claim 1 wherein said compound is (2-n-butyl-3-benzofuranyl)[4-[2-(diethylamino)ethoxyl]-3,5diiodophenyl]methane.

5. A compound according to claim 1 wherein said compound is (2-n-butyl-3-benzofuranyl)[4-[2-(diethylamino)ethoxyl]-phenyl]methane.

6. A compound according to claim 1 wherein said compound is methoxy(2-n-butyl-3-benzofuranyl)[4-[2-(diethylamino)ethoxy]-3,5-diiodophenyl]methane.

7. A compound according to claim 1 wherein said compound is methoxy(2-n-butyl-3-benzofuranyl)[4-[2-(diethylamino)ethoxy]-phenyl]methane.

8. A compound according to claim 1 wherein said compound is (2-n-butyl-3-benzofuranyl)[4-[2-(diethylamino)ethoxy]-3,5-diiodophenyl]methyl pivalate.

9. A compound according to claim 1 wherein said compound is (2-n-butyl-3-benzofuranyl)[4-[2-(diethylamino)ethoxyl]-phenyl]methyl pivalate.

* * * * *

UNITED STATES PATENT AND TRADEMARK OFFICE
CERTIFICATE OF CORRECTION

PATENT NO. : 4,806,663
DATED : February 21, 1989
INVENTOR(S) : Thomas P. Kennedy and George W. Kabalka It is certified that error appears in the above-identified patent and that said Letters Patent is hereby corrected as shown below:

Column 3, line 11, "II" should be -- III --.

Column 4, line 31, delete "salts" and insert -- acids --.

Column 4, line 61, "ethoxy" should be -- ethoxyl --.

Column 5, line 16, "ethoxy" should be -- ethoxyl --.

Column 8, line 3, "andd" should be -- and --.

Column 8, line 4, "compoun" should be -- compound --.

Signed and Sealed this

Fifteenth Day of August, 1989

Attest:

DONALD J. QUIGG

*Attesting Officer*    *Commissioner of Patents and Trademarks*